United States Patent [19]
Achter et al.

[11] Patent Number: 6,013,228
[45] Date of Patent: *Jan. 11, 2000

[54] METHOD AND SYSTEM FOR SAMPLING AND DETERMINING THE PRESENCE OF COMPOUNDS IN CONTAINERS USING A PULSED FLUORESCENCE DETECTOR

[75] Inventors: Eugene K. Achter, Lexington; Dirk Appel, Salem; David H. Fine, Sudbury; Freeman W. Fraim, Lexington, all of Mass.; Stephen J. MacDonald, Salem, N.H.

[73] Assignee: The Coca-Cola Company, Atlanta, Ga.

[*] Notice: This patent is subject to a terminal disclaimer.

[21] Appl. No.: 08/051,210

[22] Filed: Apr. 22, 1993

Related U.S. Application Data

[63] Continuation-in-part of application No. 07/890,863, Jun. 1, 1992, Pat. No. 5,352,611.

[51] Int. Cl.$^7$ .................... G01N 21/00; G01N 1/14; G01N 31/12; B07C 5/02
[52] U.S. Cl. .................... 422/66; 436/47; 436/106; 436/43; 436/172; 209/3.1; 422/80; 422/82.05; 422/82.08; 422/50; 422/93; 73/23.35
[58] Field of Search .................... 436/47, 106, 43, 436/172; 209/3.1; 422/80, 82.05, 82.08, 50, 93; 73/23.35

[56] References Cited

U.S. PATENT DOCUMENTS

| | | | |
|---|---|---|---|
| 3,826,920 | 7/1974 | Woodroffe et al. | 73/26.1 |
| 3,845,309 | 10/1974 | Heln et al. | 356/83 |
| 4,193,963 | 3/1980 | Bruening et al. | 422/52 |
| 4,469,946 | 9/1984 | Tanaka et al. | 250/373 |
| 4,541,269 | 9/1985 | Thomas | 73/23.1 |
| 4,705,669 | 11/1987 | Tsuji et al. | 422/93 |
| 4,880,120 | 11/1989 | Myers et al. | 209/3.1 |

*Primary Examiner*—Christopher L. Chin
*Assistant Examiner*—Ja-Na Hines
*Attorney, Agent, or Firm*—Birch, Stewart, Kolasch & Birch, LLP

[57] ABSTRACT

Disclosed is a method and apparatus for sampling and determining the presence of certain substances, such as residues of contaminants in containers. The method includes steps of: injecting compressed air into said containers in order to displace at least a portion of the contents thereof; evacuating a sample of the container contents so displaced by applying suction thereto; and analyzing the sample evacuated to determine the presence or absence of the certain residues therein. The compressed air is injected through a nozzle into an opening in the containers to displace a portion of the container contents and form a sample cloud outside of the container. The sample cloud is then at least partially evacuated by suction and the sample is analyzed for the presence of contaminants such as nitrogen containing compounds or hydrocarbons. The sample cloud may be split into first and second portions. Contaminants in the first portion are detected by a chemiluminescence detector and the second portion by a pulsed fluorescence detector.

1 Claim, 4 Drawing Sheets

METHOD AND SYSTEM FOR SAMPLING AND DETERMINING THE PRESENCE OF COMPOUNDS IN CONTAINERS USING A PULSED FLUORESCENCE DETECTOR

This application is a continuation-in-part of prior U.S. application Ser. No.: 07/890,863 filed Jun. 1, 1992, now U.S. Pat. No. 5,352,611 assigned to the same assignee as the present invention.

BACKGROUND OF THE INVENTION

The present invention relates to a an inspection system for sampling and determining the presence of certain substances, such as residues of contaminants within containers such as glass or plastic bottles. More specifically, the present invention relates to an improved sampling and analyzing system and method for determining the presence of substances such as residues of contaminants, as in containers such as beverage bottles rapidly moving along a conveyor past a test station in a container sorting system.

In many industries, including the beverage industry, products are packaged in containers which are returned after use, washed and refilled. Typically refillable containers, such as beverage bottles, are made of glass which can be easily cleaned. These containers are washed and then inspected for the presence of foreign matter.

Glass containers have the disadvantage of being fragile and, in larger volumes, of being relatively heavy. Accordingly, it is highly desirable to use plastic containers because they are less fragile and lighter than glass containers of the same volume. However, plastic materials tend to absorb a variety of organic compounds which may later be desorbed into the product thereby potentially adversely affecting the quality of the product packed in the container. Examples of such organic compounds are nitrogen containing compounds such as ammonia, organic nitrogen compounds, and hydrocarbons including gasoline, diesel fuel, and heating oil including aromatic hydrocarbons, such as benzenes and xylenes.

SUMMARY OF THE INVENTION

Accordingly, it is a primary object of the present invention to provide a method and system for detecting the presence or absence of specific substances—e.g., contaminants such as hydrocarbons, in materials as the materials move rapidly along a conveyor.

It is an object of the invention to provide an improved system for detecting aromatic hydrocarbons in items as the items move rapidly past a test station.

It is another object of the present invention to provide a system and method for sampling and analyzing residues in containers as they move along a conveyor without stopping the movement of the containers or impeding the movement in any way in order that high speed sampling rates of about 200 to 1000 bottles per minute may be achieved.

It is still another object of the present invention to provide a system and method for sampling and analyzing residues in containers moving along a conveyor without contacting the container being tested with any of the sampling and analyzing mechanisms.

It is yet another object of the present invention to provide a system and method for sampling and analyzing residues in containers moving along a conveyor without the physical insertion of any probes or the like into the containers.

The objects of the present invention in a preferred embodiment are fulfilled by providing a system for sampling and determining the presence of certain contaminants including nitrogen containing compounds and aromatic hydrocarbons in items moving seriatim past a test station comprising:

means for directing fluid into proximity with said item as it reaches said test station to displace vapors of contaminants;

means for evacuating a sample of vapors displaced from the item by applying suction thereto;

means for splitting the evacuated sample into first and second portions;

a chemiluminescence detector for analyzing the first portion of the sample to determine the presence or absence of contaminants of nitrogen containing compounds;

said chemiluminescence detector including,
 means for heating the first portion of the sample evacuated;
 means for mixing the heated sample portion with ozone to cause a chemical reaction therewith in order to generate chemiluminescence of the reactants; and
 means for optically analyzing said chemiluminescence to determine the presence or absence of said certain residues;

means for illuminating the second portion of the sample with radiant energy to generate fluorescence in the sample; and means for analyzing said fluorescence to determine the presence or absence of aromatic hydrocarbon contaminants in the sample.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention and wherein.

DETAILED DESCRIPTION OF PREFERRED EMBODIMENTS

Figure 1:
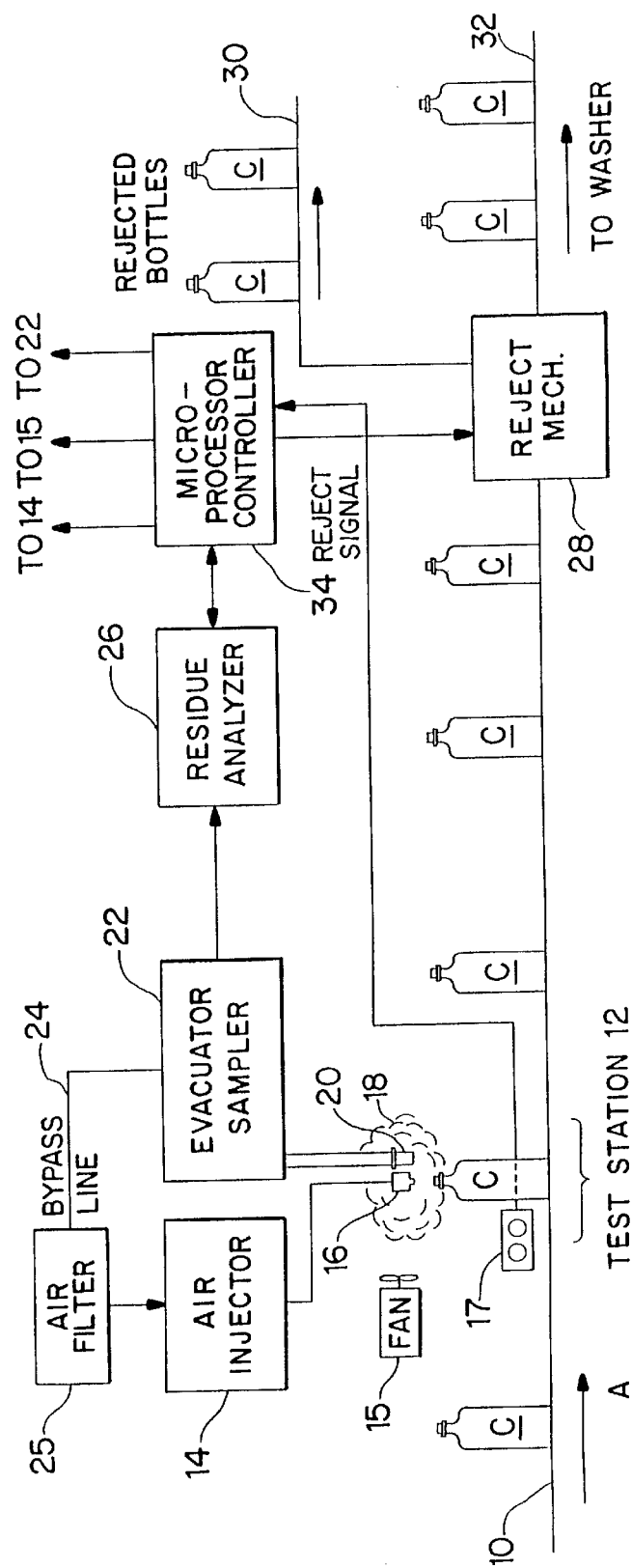
FIG. 1 is a schematic block diagram of the sampling and residue analyzing system of the present invention illustrating a plurality of containers moving seriatim along a conveyor system through a test station, reject mechanism and washer station.
Figure 2:
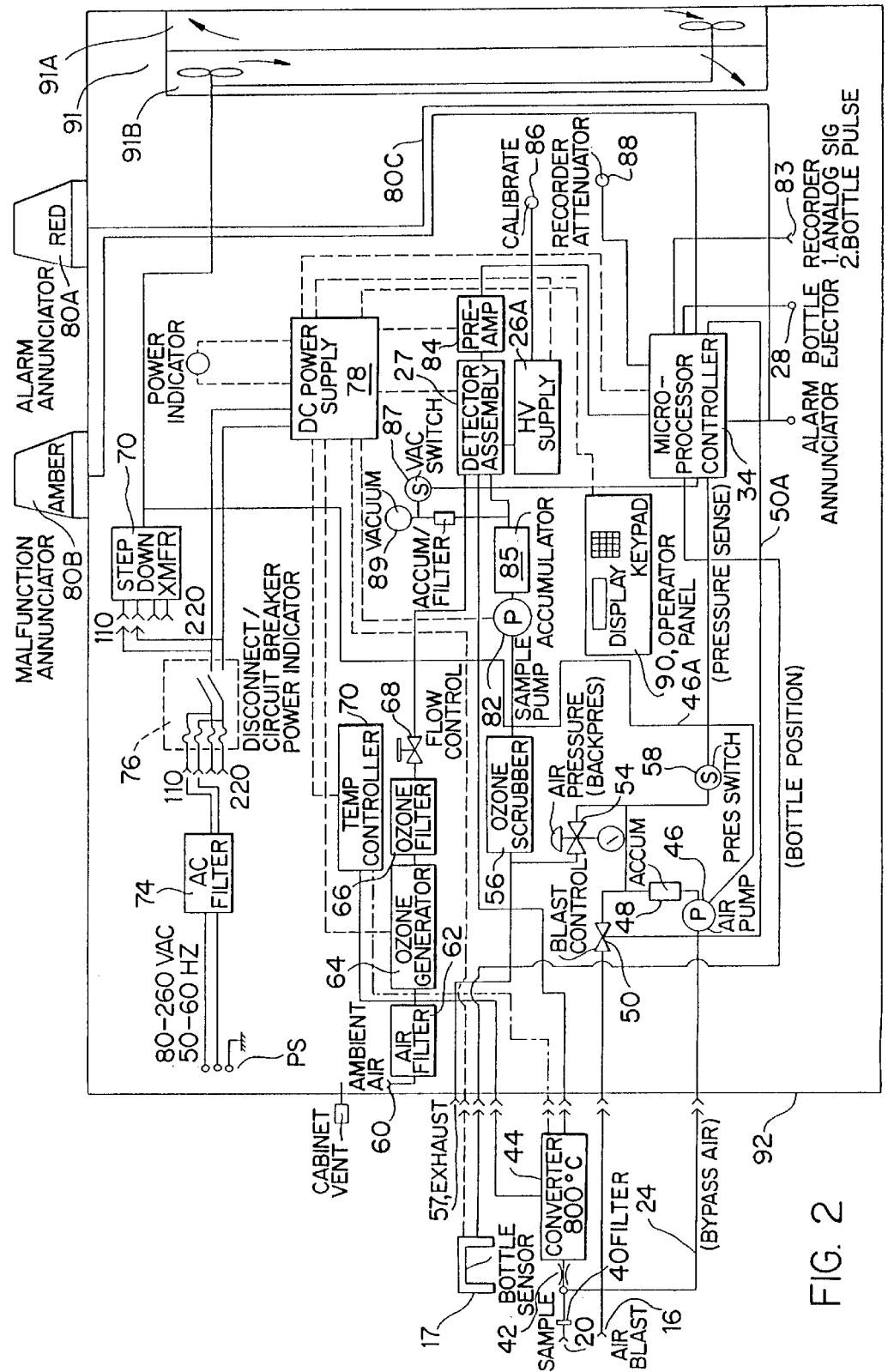
FIG. 2 is a block diagram illustrating a possible implementation of the system of FIG. 1 in a detector system in which the contaminant being detected may be a nitrogen containing compound.

The inspection system illustrated in FIGS. 1 and 2 are disclosed in parent application Ser. No.: 07/890,863 filed Jun. 1, 1992.

Referring in detail to FIG. 1 there is illustrated a conveyor 10 moving in the direction of arrow A having a plurality of uncapped, open-topped spaced containers C (e.g. plastic beverage bottles of about 1500 c.c. volume) disposed thereon for movement seriatim through a test station 12, reject mechanism 28 and conveyor 32 to a washer system. To achieve higher test rates containers C could be touching each other rather than spaced. The contents of containers C would typically include air, volatiles of residues of contaminants, if any, and volatiles of any products such as beverages which had been in the containers. An air injector 14 which is a source of compressed air is provided with a nozzle 16 spaced from but aligned with a container C at test station 12. That is nozzle 16 is disposed outside of the containers and makes no contact therewith. Nozzle 16 directs compressed air into containers C to displace at least a portion of the contents of the container to thereby emit a sample cloud 18 to a region outside of the container being tested.

As an alternative to compressed air, $CO_2$ gas could be utilized as the injected fluid. Also the compressed air or $CO_2$ gas could be heated to enhance volatility of the compounds being tested.

The column of injected air through nozzle 16 into a container C would be typically of the order of about 10 c.c. for bottle speeds of about 200 to 1000 bottles per minute. A rate of 400 bottles per minute is preferable and is compatible with current beverage bottle filling speeds. The desired test rate may vary with the size of the bottles being inspected and filled. Of course the bottles could be stationary or moving slower than 200 bottles per minute and the system would still work. Only about 10 c.c. of the container contents would be displaced to regions outside of the bottle to form sample cloud 18.

Also provided is an evacuator sampler 22 which may comprise a vacuum pump or the like coupled to a sampling tube or conduit 20. The tube is mounted near, and preferably downstream (e.g., about 1/16 inch) of the air injector 14 so as to be in fluid communication with sample cloud 18 adjacent to the opening at the top of containers C.

Neither nozzle 16 nor tube 20 contacts the containers C at test station 12; rather both are spaced at positions outside of the containers in close proximity to the openings thereof. This is advantageous in that no physical coupling is required to the containers C, or insertion of probes into the containers, which would impede their rapid movement along conveyor 10 and thus slow down the sampling rate. High speed sampling rates of from about 200 to 1000 bottles per minute are possible with the system and method of the present invention. The conveyor 10 is preferably driven continuously to achieve these rates without stopping or slowing the bottles down at the test station.

A bypass line 24 is provided in communication with the evacuator sampler 22 so that a predetermined portion (preferably about 90%) of the sample from cloud 18 entering tube 20 can be diverted through bypass line 24. The remaining sample portion passes to a residue analyzer 26, which determines whether specific substances are present, and then is exhausted. One purpose of diverting a large portion of the sample from cloud 18 is to reduce the amount of sample passing from evacuator sampler 22 to residue analyzer 26 in order to achieve high speed analysis. This is done in order to provide manageable levels of samples to be tested by the residue analyzer 26. Another purpose for diverting a portion of the sample is to be able to substantially remove all of sample cloud 18 by evacuator 22 from the test station area and divert the excess through bypass line 24. In a preferred embodiment the excess portion of the sample passing through bypass line 24 returned to air injector 14 for introduction into the subsequent containers moving along conveyor 10 through nozzle 16. However, it would also be possible to simply vent bypass line 24 to the atmosphere.

It should be understood that sample cloud 18 could be analyzed in situ without transporting it to a remote analyzer such as 26. It could also be transported to analyzer 26 by blowing rather than sucking.

A microprocessor controller 34 is provided for controlling the operation of air injector 14, evacuator sampler 22, residue analyzer 26, a reject mechanism 28 and an optional fan 15. Container sensor 17 including juxtaposed radiation source and photodetector is disposed opposite a reflector (not shown) across conveyor 10. Sensor 17 tells controller 34 when a container arrives at the test station and briefly interrupts the beam of radiation reflected to the photodetector. Optional fan 15 is provided to generate an air blast towards sample cloud 18 and preferably in the direction of movement of containers C to assist in the removal of sample cloud 18 from the vicinity of test station 12 after each container C is sampled. This clears out the air from the region of the test station so that no lingering residues from an existing sample cloud 18 can contaminate the test station area when successive containers C reach the test station for sampling. Thus, sample carryover between containers is precluded. The duty cycle for operation of fan 15 is controlled by microprocessor 34 as indicated diagrammatically in FIG. 1. Preferably fan 15 is continuously operating for the entire time the rest of the system is operating.

A reject mechanism 28 receives a reject signal from microprocessor controller 34 when residue analyzer 26 determines that a particular container C is contaminated with a residue of various undesirable types. Reject mechanism 28 diverts contaminated rejected bottles to a conveyor 30 and allows passage of uncontaminated, acceptable bottles to a washer (not shown) on a conveyor 32.

An alternative option is to place the bottle test station downstream of the bottle washer in the direction of conveyor travel, or to place an additional test station and sample and residue analyzing system after the washer. In fact it may be preferable to position the test station and system after the washer when inspecting bottles for some contaminants. For example, if the contaminant is a hydrocarbon, such as gasoline which is insoluble in water, it is easier to detect residues of hydrocarbon after the bottles have been washed. This is because during the washing process in which the bottles are heated and washed with water, water soluble chemical volatiles are desorbed from the bottles by the heating thereof and then dissolved in the washing water. Certain hydrocarbons, on the other hand, not being water soluble, may then be sampled by a sampler 22 downstream of the washer, to the exclusion of the dissolved, water-soluble chemicals. Therefore, the detection of such hydrocarbons can be performed without potential interference from other water soluble chemicals if the bottles pass through a washer before testing.

Referring to FIG. 2 there is illustrated a specific embodiment of a nitrogen compound detector system for use with the sampling and analyzing system of FIG. 1 wherein like reference numerals refer to like parts. As illustrated, a nozzle 16 is provided for generating an air blast which passes into a container (not shown) being inspected. The air passing through nozzle 16 may be heated or unheated it being advantageous to heat the air for some applications. Juxtaposed to the nozzle 16 is sample inlet tube 20 including a filter 40 at the output thereof for filtering out particles from the sample. Suction is provided to tube 20 from the suction side of pump 82 connected through an analyzer 27.

A portion of the sample (for example, 90–95% of a total sample flow of about 6000 c.c. per minute), as described in connection with FIG. 1, is diverted through a bypass line 24 by means of connection to the suction side of a pump 46. Pump 46 recirculates the air through an accumulator 48, a normally open blast control valve 50, and back to the air blast output nozzle 16. A backpressure regulator 54 helps control pressure of the air blast through nozzle 16 and vents excess air to exhaust 57. Blast control valve 50 receives control signals through line 50A from microprocessor controller 34 to normally maintain the valve open to permit the flow of air to the nozzle.

Electrical power is provided to pump 46 via line 46A coupled to the output of circuit breaker 76 which is in turn coupled to the output of AC filter 74 and AC power supply PS.

The detector assembly 27 in the embodiment of FIG. 2 is an analyzer which detects the residue of selected compounds such as nitrogen containing compounds in the containers being inspected by means of a method of chemiluminescence. This type of detector is generally known and includes a chamber for mixing ozone with nitric oxide, or with other compounds which react with ozone, in order to allow them to react, a radiation-transmissive element (with appropriate filter), and a radiation detector to detect chemiluminescence from the products of reaction. For example, when NO, produced from heating nitrogen compounds (such as ammonia) in the presence of an oxidant (e.g. oxygen in air), chemically reacts with the ozone, characteristic light emission is given off at predetermined wavelengths such as wavelengths in the range of about 0.6 to 2.8 microns. Selected portions of the emitted radiation of chemiluminescence, and its intensity, can be detected by a photomultiplier tube.

Accordingly, in the system of FIG. 2 ambient air is drawn in through intake 60 and air filter 62 to an ozone generator 64. Ozone is generated therein, as by electrical discharge into air, and is output through ozone filter 66 and flow control valve 68 to the detector assembly 27 wherein it is mixed with samples from containers input through intake tube 20, filter 40, flow restrictor 42, and converter 44. The sample from intake tube 20 is passed through a converter 44, such as an electrically-heated nickel tube, in which the temperature is raised to approximately 800° C. to 900° C. before being input to detector assembly 27. Temperatures in the range of 400° C. to 1400° C. may also be acceptable. When nitrogen-containing compounds such as ammonia are so heated, NO (nitric oxide) is produced, and the nitric oxide is supplied to the chamber of the detector assembly 27. Compounds other than NO which may react with $O_3$ and chemiluminescence may also be produced in converter 44 e.g., organic compounds derived from heating of gasoline or cleaning residue.

A temperature controller 70 supplied with electrical power through a transformer 72 is used to control the temperature of converter 44.

The samples in the detector assembly 27 after passage through its chamber are output through an accumulator 85 and pump 82 to an ozone scrubber 56, and to an exhaust output 57 in order to clear the residue detector for the next sample from the next container moving along the conveyor 10 of FIG. 1. (As indicated above, an (optional) fan, not shown in FIG. 2, may be employed to help clear any remaining sample cloud from near the sample inlet tube 20.) Outputs from detector assembly 27 relating to the results of the tests are output through a preamp 84 to microprocessor 34 which feeds this information in an appropriate manner to a recorder 83. The recorder 83 is preferably a conventional strip recorder, or the like, which displays signal amplitude vs. time of the sample being analyzed.

The microprocessor 34 may be programmed to recognize, as a "hit" or the detection of a specific residue, a signal peak from a photodetector of the detector assembly 27 which is present in a predetermined time interval (based on the sensed arrival of a container at the test station) and whose slope and amplitude reach predetermined magnitudes and thereafter maintain such levels for a prescribed duration.

The microprocessor controller 34 also has an output to a bottle rejector 28 to reject contaminated bottles and separate them from bottles en route to a washer.

A calibration terminal 86 is provided for residue analyzer 27 for adjusting the high voltage supply 26A associated with the detector assembly. Also provided is a recorder attenuator input terminal 88 connected to the microprocessor controller 34 for adjusting the operation of the recorder. Detector assembly 27 receives electrical power from the high voltage supply 26A.

Additional controls include operator panel 90 including a key pad and display section permitting an operator to control the operation of the detector assembly 27 in an appropriate fashion.

DC power is supplied to all appropriate components through DC power supply 78 coupled to the output of power supply PS.

An optional alarm enunciator 80A is provided for signaling an operator of the presence of a contaminated container. Alarm enunciator 80A is coupled to the output of microprocessor controller 34 via output control line 80C. A malfunction alarm 80B is also coupled to microprocessor controller 34 for receiving fault or malfunction signals such as from pressure switch 58 or vacuum switch 87 when pressures are outside of certain predetermined limits.

Other safety devices may be provided such as vacuum gauge 89, and back pressure control valve 54 for ensuring proper operation of the system.

Most components of the entire system of FIG. 2 are preferably enclosed in a rust-proof, stainless steel cabinet 92. The cabinet is cooled by a counter-flow heat exchanger 91 having hermetically separated sections 91A and 91B in which counter air flow is provided by appropriate fans.

The system illustrated in FIG. 2 is housed within a stainless steel rectangular cabinet 92 for enclosing the majority of the components of FIG. 2 in a hermetically sealed environment.

Other forms of high speed analyzers, such as electron capture detectors or photoionization detectors, may be suitable in place of the chemiluminescence analyzer described with reference to FIG. 2. One preferred detector is a pulsed fluorescence gas analyzer of the type described in U.S. Pat. No. 3,845,309 (Helm et al), whose disclosure is incorporated herein by reference to that patent. In such analyzers gaseous samples drawn into a chamber and illuminated by radiant energy from a flash-tube fluoresce and emit radiation which is detected by a photodetector. As set forth in more detail hereafter, it has been found that an analyzer of the type referred to in the '309 patent, such as a Model 43 Pulsed Fluorescence $SO_2$ Analyzer available from Thermo Environment Instruments, Inc. of Franklin, Mass., when modified by removal of physical/chemical filters, becomes a highly sensitive detector of certain hydrocarbons such as polycyclic aromatic hydrocarbons present in gasoline and other petroleum products. The modified fluorescent gas analyzer may be used as the residue analyzer 26 in the systems of FIG. 1 and FIG. 2 (in the latter system no ozone generator 64 or ozone-handling components would be needed, and preferably a converter 44 would also be unnecessary.)

Also, the sample sucked into the tube 20 may be separated into two or more streams and input to a plurality of analyzers rather than the single analyzer 26 shown in FIG. 1, with each analyzer 26 being used to detect different types of contaminants. It is also possible to use as one or more of the analyzers a different type of analyzers than analyzer 27 (FIG. 2) which pretreats the sample in converter 44. In that case, if analyzer 27 is employed to detect contaminants in one stream, part of the sample would be routed to the different type of analyzer and part to converter 44.

In addition the materials to be inspected are not limited to substances in containers. For example, the method and system of the present invention could be used to detect volatiles adsorbed in shredded strips or flakes of resins, or plastic stock to be recycled for manufacturing new plastic beverage bottles. This shredded or flaked plastic stock could be placed directly on a conveyor belt 10 and passed through test station 12 of FIG. 1; or the plastic stock could be placed in baskets, buckets or other types of containers disposed thereon and inspected in batches.

Other materials which could be inspected according to the method and system of the invention include various foodstuffs such as fish being monitored for amines, pharmaceutical products and herbicides being checked for reagents, rubber products such as tires being monitored for chemicals such as blowing agents, web materials such as paper in a paper mill being checked for acids, and even clothing worn by persons being inspected for volatile compounds such as explosives or drugs. Such materials may be inspected while passing through a test station on a conveyor, either within open containers or in the absence of containers. In the latter case high flow rates and/or heating of the compressed air or other fluid directed at the material by the nozzle 16 may be in order to obtain desired samples of the volatile substances to be detected.

Still further the bottles being tested may be new bottles that have never been filled with a beverage. Thus, new bottles could be tested for excessive acid aldehyde content, which may be a byproduct of the manufacturing process.

In the system of FIG. 2, a suction pump or by-pass pump 46 is used to pull approximately 8 liters/minute of sample air into a sampling head and past the inlet tubes 20 of the chemiluminescence subsystems. Two chemiluminescence subsystems may also be employed, each aspirating 0.25 to 0.5 liters/minute of air sample through flow lines (split from tube 20) and preferably through separate converters. The rest of the 8 liters/minute passes through the by-pass pump 46 and is not analyzed.

The intended purpose of the system of FIG. 2 is to detect a variety of contaminants, including nitrogen compounds such as salts of ammonia and amines, and hydrocarbons such as gasoline, diesel fuel, and heating oil, in returned plastic beverage bottles on a conveyor. In a two subsystem arrangement one of the chemiluminescence channels may be selective for the detection of nitrogen compounds; the other responds to a variety of hydrocarbons.

Figure 3:
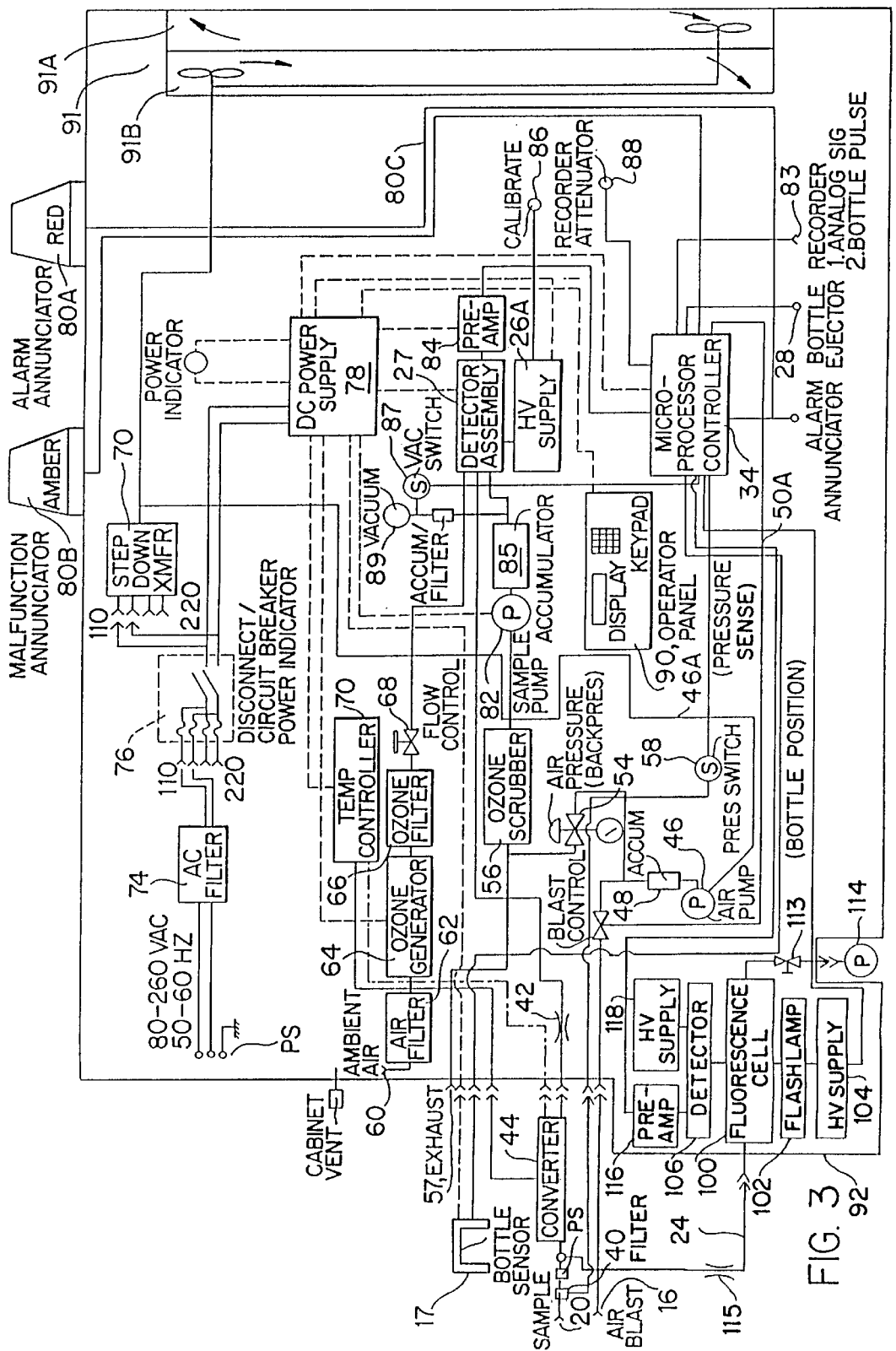
FIG. 3 is a schematic block diagram similar to FIG. 2 with the addition of a pulsed fluorescence detector sub-assembly.

The detection system illustrated in FIG. 3 is a two subsystem arrangement which includes pulsed fluorescence enhancements to provide increased response to aromatic hydrocarbons, such as benzenes and xylenes, that occur in petroleum products such as gasoline, diesel fuel, and heating oil, without interference from residues of the beverage products such as carbonated colas.

With reference to FIG. 3, a pulsed fluorescence detector assembly is disposed between the by-pass line 24 and a vacuum pump 114. The pump 114 is typically quite large and rests on the floor outside of cabinet 92. Flow from sample inlet 20 is split between converter 44 leading to chemiluminescence detector assembly 27 and line 24 to the pulsed fluorescence detector assembly.

The pulsed fluorescence detector assembly includes a fluorescence cell 100, a flash lamp 102, a high voltage supply 104 connected between the flash lamp 102 and controller 34, a photomultiplier detector 106 connected to cell 100, a pre-amp connected between detector 106 and controller 34, and a high voltage supply for the detector 106. The vacuum pump 114 draws sample vapors along line 24 through a flow restrictor 115 and cell 100 to exhaust.

A line from pressure switch 58 to a pressure sensor PS in the sample inlet line 20 just downstream of filter 40 feeds a signal from that sensor to switch 58.

Figure 4:
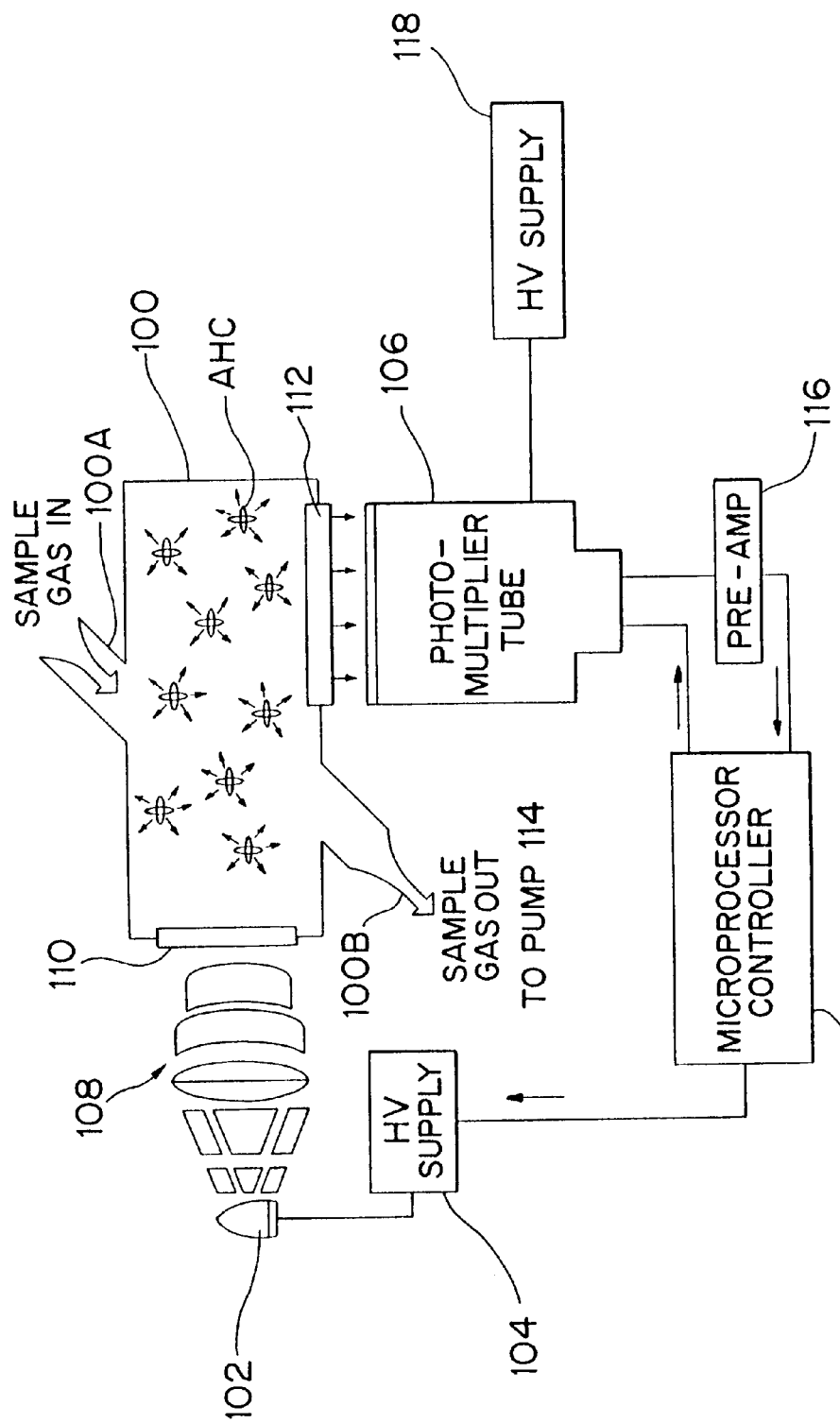
FIG. 4 is a schematic illustration of details of the pulsed fluorescence detector sub-assembly of FIG. 3.

Operation of the pulsed fluorescence detector assembly of FIG. 3 can be readily understood by reference to the more detailed showing in FIG. 4 of the detector assembly and its connections to the microprocessor 34. Excitation wavelengths for a xenon flash lamp 102 and detection wavelengths of the fluorescing sample are chosen to optimize sensitivity and selectivity for aromatic hydrocarbons, and to avoid detecting beverage product residues. Preferred excitation wavelengths of radiation from lamp 102 are chosen to be approximately 205 nanometers by passing the radiation emitted by the xenon flash lamp through optic assembly 108 and a bandpass filter 110. The wavelength of radiation passing to photomultiplier 106 is limited to about 320 nanometers by a bandpass filter 112 .

Pulsed bursts of radiation entering cell 100 through filter 110 impinge upon aromatic hydrocarbon (AHC) vapor molecules, and excite those molecules causing them to fluoresce. Radiation of wavelength about 320 nanometers is detected by photomultiplier 106, and this information is processed in microprocessor controller 34 to determine the presence and quantities of these aromatic hydrocarbons in the sample. A control signal can then be generated to reject contaminated containers in a system such as illustrated in FIG. 1.

A pulsed fluorescence detector assembly of the type generally described and illustrated in connection with FIG. 4 is similar to a commercially available unit manufactured and sold by Thermo Environment Instruments Inc. of Franklin, Mass. as a "Model 43 Pulsed Fluorescence $SO_2$ Analyzer"; however, with modifications to detect aromatic hydrocarbons rather than $SO_2$ (sulfur dioxide).

The sample inlet system to the cell 100 includes an orifice of inner diameter about 0.04 cm to 0.3 cm, connected to the optical cell 100 at 100A by metal tube of typical inner diameter 0.6 cm and typical length 1 meter. Downstream of the optical cell 100 is a throttle valve 113 leading to vacuum pump 114 with typical displacement 150 to 300 liters/minute.

The diameter of the inlet orifice and the setting of the throttle valve 113 may be adjusted to achieve a typical mass flow rate through the cell 100 of 3 to 20 standard liters/ minute at a cell pressure of 0.03 to 0.3 atmospheres. This mass flow rate also satisfies the requirements for the by-pass pump 114 and does not adversely affect the flow through, and performance of the chemiluminescence subsystem of FIG. 3.

The pulsed fluorescence subsystem of FIG. 3 has been found to provide sensitivity to aromatic hydrocarbons about 100 times greater than that of the chemiluminescence-based system of FIG. 20. Discrimination against product residues of carbonated beverages is also extremely effective. Under conditions where a trace level of aromatic hydrocarbon gives a signal to noise ratio of 100, the signal from beverage product volatiles is virtually indistinguishable from background noise.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method of sampling and determining the presence of certain substances in a container comprising the steps of:

injecting fluid into an opening in said container in order to displace at least a portion of the contents thereof to form a sample cloud at regions outside of the container adjacent the opening thereof;

evacuating a sample of said portion of the container contents so displaced by applying suction to the sample cloud in said regions outside of the container;

splitting the sample evacuated into first and second portions;

providing a chemiluminescence detector for analyzing the first portion of the sample to determine presence or absence of contaminants of nitrogen containing compounds;

said chemiluminescence detector including,
means for heating the first portion of the sample evacuated; and
means for mixing the heated sample portion with ozone to cause a chemical reaction therewith in order to generate chemiluminescence of the reactants;

optically analyzing said chemiluminescence to determine presence or absence of said certain substances;

illuminating the second portion of the sample with radiant energy to generate fluorescence in the sample; and analyzing said fluorescence to determine presence or absence of aromatic hydrocarbon contaminants in the sample.

* * * * *